United States Patent [19]

Sugimoto

[11] Patent Number: 5,188,110
[45] Date of Patent: Feb. 23, 1993

[54] METHOD AND APPARATUS FOR SETTING MULTI-SLICE IMAGING CONDITIONS IN COMPUTED TOMOGRAPHIC IMAGING SYSTEMS

[75] Inventor: Hiroshi Sugimoto, Nasu, Japan

[73] Assignee: Kabushiki Kaisha Toshiba, Kawasaki, Japan

[21] Appl. No.: 646,930

[22] Filed: Jan. 28, 1991

Related U.S. Application Data

[63] Continuation-in-part of Ser. No. 378,623, Jul. 12, 1989, abandoned.

[30] Foreign Application Priority Data

Jul. 13, 1988 [JP] Japan .................. 63-174380

[51] Int. Cl.⁵ .................................. A61B 6/03
[52] U.S. Cl. .......................... 128/653.1; 378/20; 378/206
[58] Field of Search ............... 128/653.1; 378/4, 9, 378/17, 20, 206; 324/318, 322

[56] References Cited

U.S. PATENT DOCUMENTS

| | | | |
|---|---|---|---|
| 4,117,337 | 9/1978 | Staats | 378/20 |
| 4,242,587 | 12/1980 | Lescrenier | 378/206 |
| 4,296,329 | 10/1981 | Mirabella | 378/20 |
| 4,426,726 | 1/1984 | Cheetham | 378/206 |
| 4,442,533 | 4/1984 | Lescrenier | 378/206 |
| 4,538,289 | 8/1985 | Scheibengraber | 378/20 |
| 4,624,007 | 11/1986 | Muranushi | 378/4 |
| 4,702,257 | 10/1987 | Moriyama et al. | 128/653.1 |
| 5,018,178 | 5/1991 | Katsumata | 378/4 |
| 5,080,100 | 1/1992 | Trotel | 128/653.1 |
| 5,142,559 | 8/1992 | Wielopolski et al. | 378/206 |

Primary Examiner—Lee S. Cohen
Assistant Examiner—Krista M. Pfaffle
Attorney, Agent, or Firm—Cushman, Darby & Cushman

[57] ABSTRACT

A method and an apparatus of setting multi-slice imaging conditions in computed tomographic imaging systems capable of taking a desired multi-slice imaging in a desired imaging region without scanning imaging. In the method and apparatus, an object to be imaged is illuminated along at least one projection plane and within at least one projection area corresponding to an imaging region; the projection area is changed and detected; one of the multi-slice imaging conditions including an imaging time interval, a slice thickness, and a number of slices is specified; and a remaining part of the multi-slice imaging conditions is determined in accordance with the part of the multi-slice imaging conditions specified by the specifying means and the detected projection area.

12 Claims, 7 Drawing Sheets

METHOD AND APPARATUS FOR SETTING MULTI-SLICE IMAGING CONDITIONS IN COMPUTED TOMOGRAPHIC IMAGING SYSTEMS

This is a continuation-in-part application of our earlier copending, commonly assigned application Ser. No. 378,623 filed Jul. 12, 1989, which is now abandoned.

BACKGROUND OF THE INVENTION

1. Field of the Invention

The present invention relates to computed tomographic imaging such as a nuclear magnetic resonance imaging and, more particularly, to computed tomographic imaging capable of a multi-slice imaging in which imagings are carried out at a plurality of slicing positions equidistantly apart.

2. Description of the Background Art

Conventionally, a nuclear magnetic resonance imaging apparatus typically has a configuration shown in FIG. 1, where it is shown to be comprised of a frame 1 containing an imaging system, and a bed 2 for carrying a patient 3. The bed 2 has a slidable top plate 4 over which the patient 3 is placed, and a lift 5 for adjusting the height of the top plate 4. The frame 1 has a bore 1A into which the top plate 4 is to be slid in, a first projector 6 for illuminating a side of the patient 3 at the opening of the bore 1A, a second projector 7 for illuminating a top of the patient 3 at the opening of the bore 1A, and a control panel 8 for manually controlling the sliding of the top plate 4 into the bore 1A.

The illuminations by the first and second projectors 6 and 7 are provided for the purpose of determining the position of a part of the patient 3 to be imaged. As shown in FIG. 2, the first projector 6 projects a cross-shaped beam 6B along an X axis. This X-directed beam can be inclined by an angle $\theta x$ causing the beam to move in a Y-direction across the side of the patient 3. The second projector 7 projects a cross-shaped beam 7B in a Y direction.

In taking a multi-slice image, the top plate 4 and the lift 5 are adjusted such that the center of the part of the patient 3 to be imaged meets with the centers of the cross-shaped beams 6B (X cross-shaped beam) and 7B (Y cross-shaped beam). The X cross-shaped beam 6B must be inclined in the Y-direction when the height of the top plate 4 is insufficient because of some structural limitation, or when desired slice image is transverse to the sagittal plane (Y-Z plane).

Then, as shown in FIG. 3, the slicing angle and the positions of the centers of the X and Y cross-shaped beams measured by potentiometers in the first projector 6 is transmitted to a control unit 10 so as to obtain a display on a display unit 11. The second projector 7 does not produce any signal since it has a fixed position. After the patient 3 has been carried into the bore 1A, the other parameters required for the single-slice imaging such as a type of slicing plane, i.e., a sagittal plane (Y-Z plane), a coronal plane (X-Z plane), or an axial plane (X-Y plane), as well as the multi-slice imaging conditions such a number of slices, a slice thickness, and an imaging time interval TR for receiving nuclear magnetic resonance signals will be entered manually from an operation unit 9.

Then, a quick single-slice imaging called a scanner image will be taken. This scanner image is taken along a plane which is perpendicular to the plane to be used for the multi-slice imaging. The precise positions of each of the multi-slices of the object image can be determined from this scanner image. For this reason, the imaging conditions for this scanner image are set such that it can be done in a short time (less than a few minutes), and sufficient image quality can be obtained for precisely determining the positions of the multi-slices. To accomplish this quick scanner image, picture elements are made to be coarser and multiplicity of data reading is reduced.

After the scanner imaging, the imaging conditions required for the multi-slice imaging such as a number of slices, a slice thickness, and an imaging time interval TR, as well as the imaging parameters required for the multi-slice imaging such as a view field, a coarseness of picture elements, a multiplicity of data reading, slice positions, and a slice angle are entered manually from the operation unit 9.

Here, when the number of slices is made larger and at the same time the imaging time interval TR is made longer, the nuclear magnetic resonance signals received weaken substantially, so that the image quality is severely damaged. Thus, once the imaging time interval TR is given the maximum number of slices can be automatically determined to achieve a satisfactory level of image quality, and vice versa. The number of slices and the slice thickness selected within this limitation will then determine the desired imaging region. For example, when the slice thickness is 10 mm and the number of slices is 10, the desired imaging region has a thickness of 100 mm.

However, since the scanner imaging is limited by the view field used, it has often been the case that an entire imaging region determined on a basis of the desired positions and angles of the multi-slice is too large to be imaged by the scanner in a single operation. In other words, proper fitting of the imaging region into the scanner image has conventionally depended on the experience and skill of an operator. In particular, since the relation and skill of an operator. In particular, since the relation between the imaging region and the imaging time interval TR has conventionally been obscure to the operator, such a proper fitting of the imaging region into the scanner image has been a difficult task, so that re-taking of the scanner image has often been necessary.

Furthermore, at the time of positioning the patient 3 it has not been possible to know the maximum number of slices which may be imaged.

SUMMARY OF THE INVENTION

It is therefore an object of the present invention to provide a method and an apparatus for setting multi-slice imaging conditions in a computed tomographic imaging system which allows the taking of a desired multi-slice image in a desired imaging region without requiring an initial scanning image for setting the scanning conditions.

It is also an object of the present invention to provide such a method and an apparatus for setting the above-mentioned multi-slice imaging conditions in which the relation between the imaging region and the imaging time interval becomes apparent to the operator before taking images.

According to one aspect of the present invention there is provided an apparatus for setting multi-slice imaging conditions in a computed tomographic imaging system, comprising: projector means for illuminating an object to be imaged within at least one projection area defined along at least one projection plane, said projection plane and said projection area corresponding to an imaging region; projection area changing means for changing the projection area; projection area detecting means for detecting the projection area; input means for specifying one of the multi-slice imaging conditions including an imaging time interval, a slice thickness, and a number of slices; and processing means for determining a remaining part of the multi-slice imaging conditions in accordance with the part of the multi-slice imaging conditions specified by the specifying means and the detected projection area.

According to another aspect of the present invention there is provided a method of setting multi-slice imaging conditions in a computed tomographic imaging system, comprising the steps of: illuminating an object to be imaged within at least one projection area defined along at least one projection plane, said projection plane and projection area corresponding to an imaging region; changing the projection area; detecting the projection area; specifying one of the multi-slice imaging conditions including an imaging time interval, a slice thickness, and a number of slices; and determining a remaining part of the multi-slice imaging conditions in accordance with the part of the multi-slice imaging conditions specified by the specifying means and the detected projection area.

Other features and advantages of the present invention will become apparent from the following description taken in conjunction with the accompanying drawings.

DETAILED DESCRIPTION OF THE PREFERRED EMBODIMENTS

Figure 1:
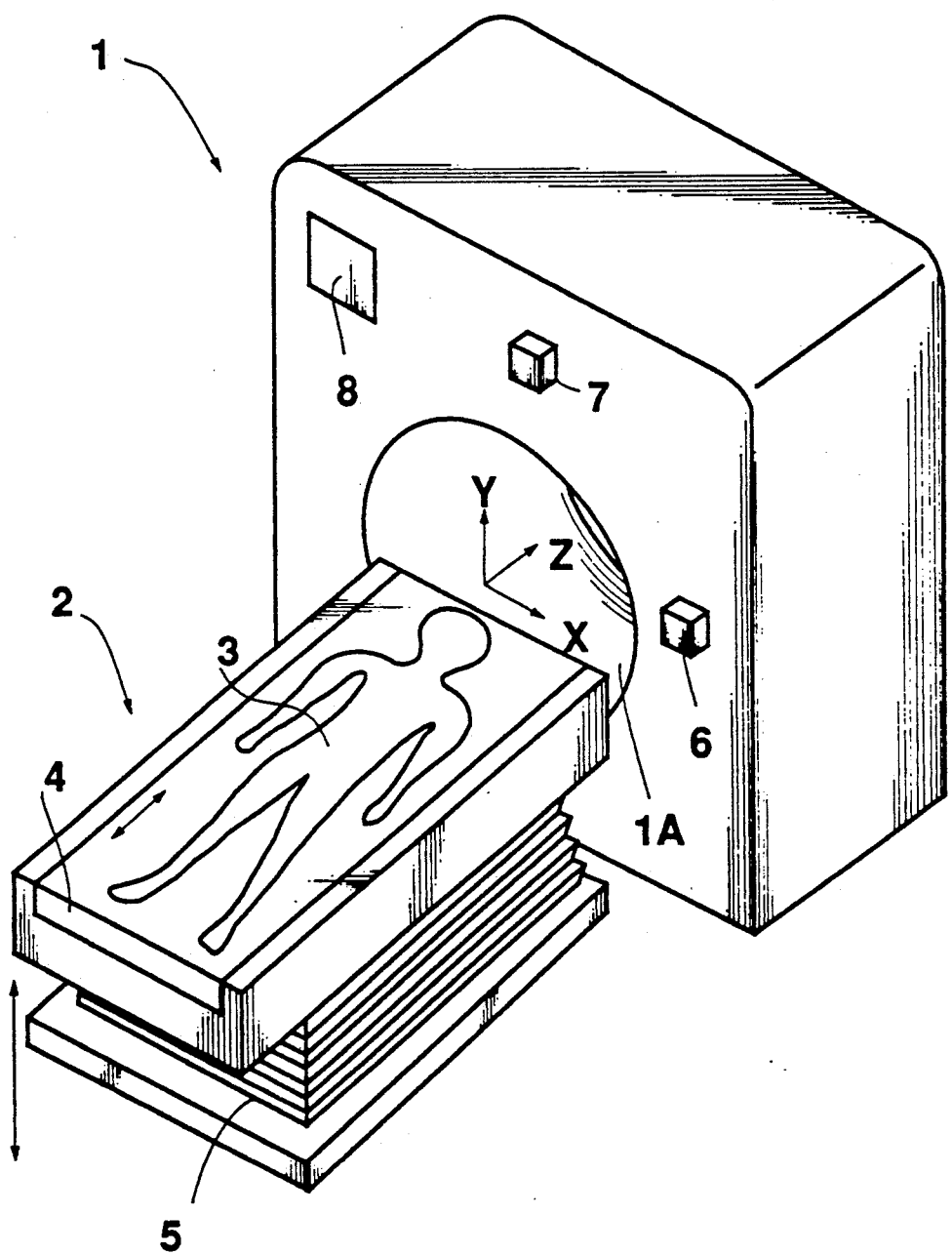
FIG. 1 is a schematic perspective view of a conventional computed tomographic imaging system featuring a conventional apparatus for setting multi-slice imaging conditions.
Figure 2:
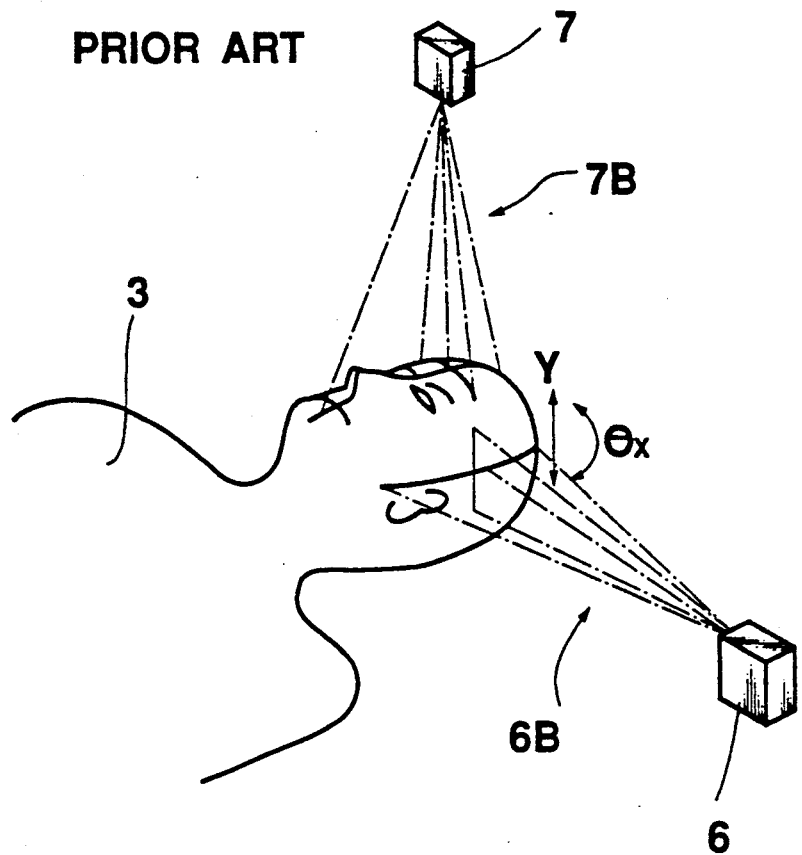
FIG. 2 is an illustration of the operation of the apparatus for setting multi-slice imaging conditions in the conventional computed tomographic imaging system of FIG. 1.
Figure 3:
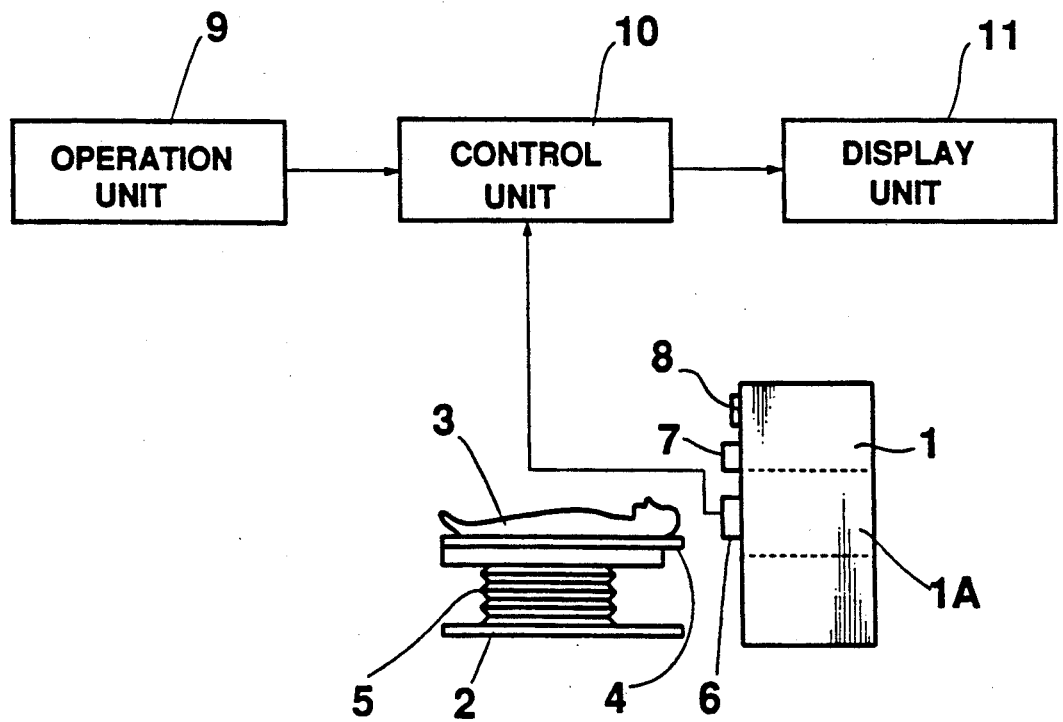
FIG. 3 is a schematic diagram of the conventional computed tomographic imaging system of FIG. 1.
Figure 4:
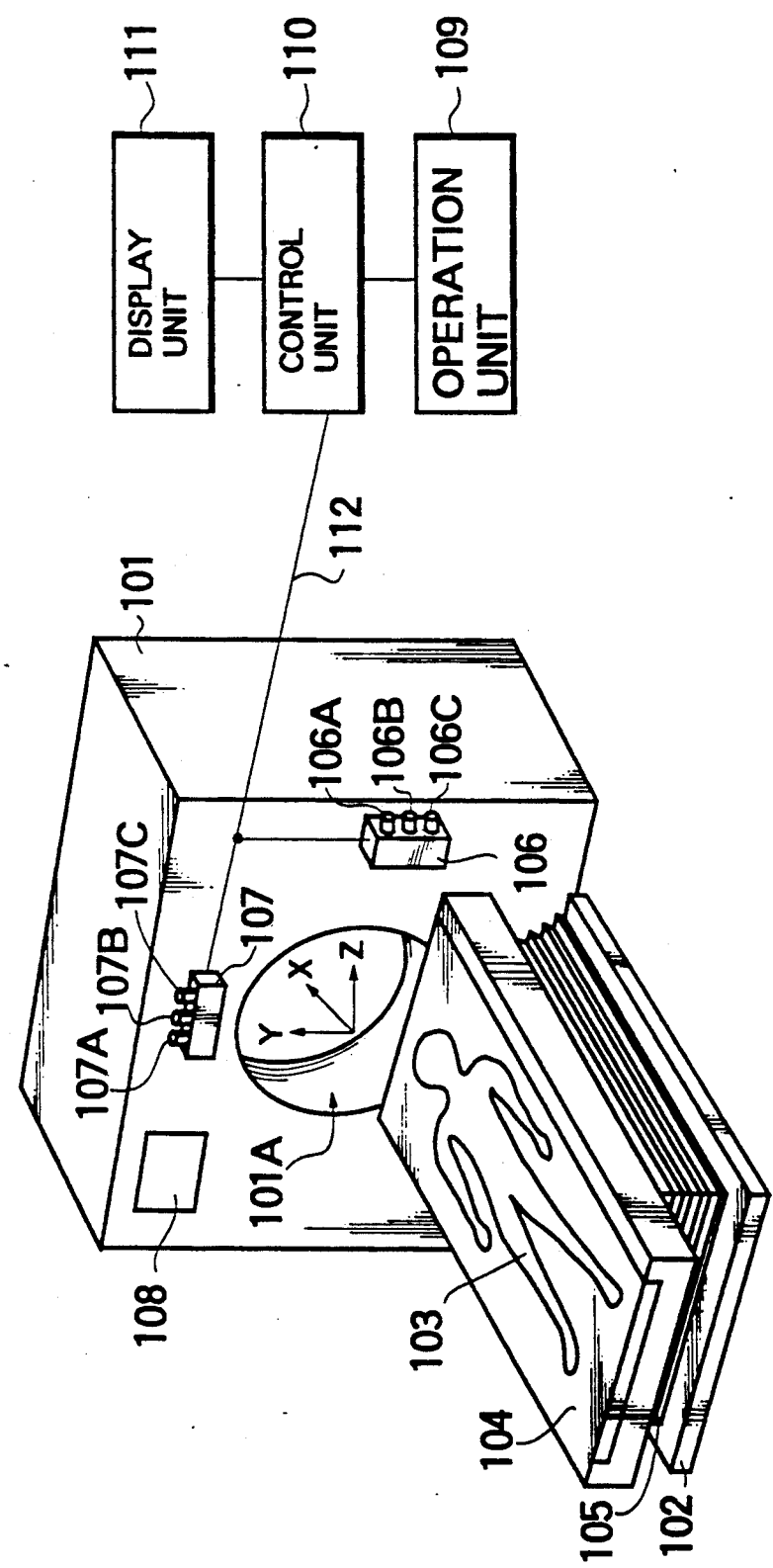
FIG. 4 is a schematic partially diagrammatic perspective view of one embodiment of an apparatus for setting multi-slice imaging conditions according to the present invention.

Referring now to FIG. 4, one embodiment of an apparatus according to the present invention for setting multi-slice imaging conditions in a computed tomographic imaging system will be described.

In this embodiment, the system comprises a frame 101 containing an imaging system, and a bed 102 for carrying a patient 103. The bed 102 has a slidable top plate 104 over which the patient 103 is placed and a lift 105 for adjusting height of the top plate 104. The frame 101 has a bore 101A into which the top plate 104 is to be slid in, a first projector 106 for illuminating a side of the patient 103 at an opening of the bore 101A, a second projector 107 for illuminating a top of the patient 103 at the opening of the bore 101A, and a control panel 108 for manually controlling the sliding of the top plate 104 into the bore 101A. The system further comprises an operation unit 109 for manual entering of imaging conditions and parameters, a control unit 110 for controlling the imaging process in accordance with the manually entered imaging conditions and parameters, a display unit 111 for displaying the images taken, and a transmission line 112 for transmitting signals between the control unit 110 and the first and second projectors 106 and 107.

As can be seen in a perspective view of the frame 101 shown in FIG. 4, the first projector 106 has three knobs for controlling illuminating beam of the first projector 106, including a first projection area changing knob 106A, a first projection moving knob 106B, and a first projection inclining knob 106C, all of which will be described in detail below. Likewise, the second projector 107 has three knobs for controlling illuminating beam of the second projector 107, including a second projection area changing knob 107A, a second projection moving knob 107B, and a second projection inclining knob 107C.

Figure 5:
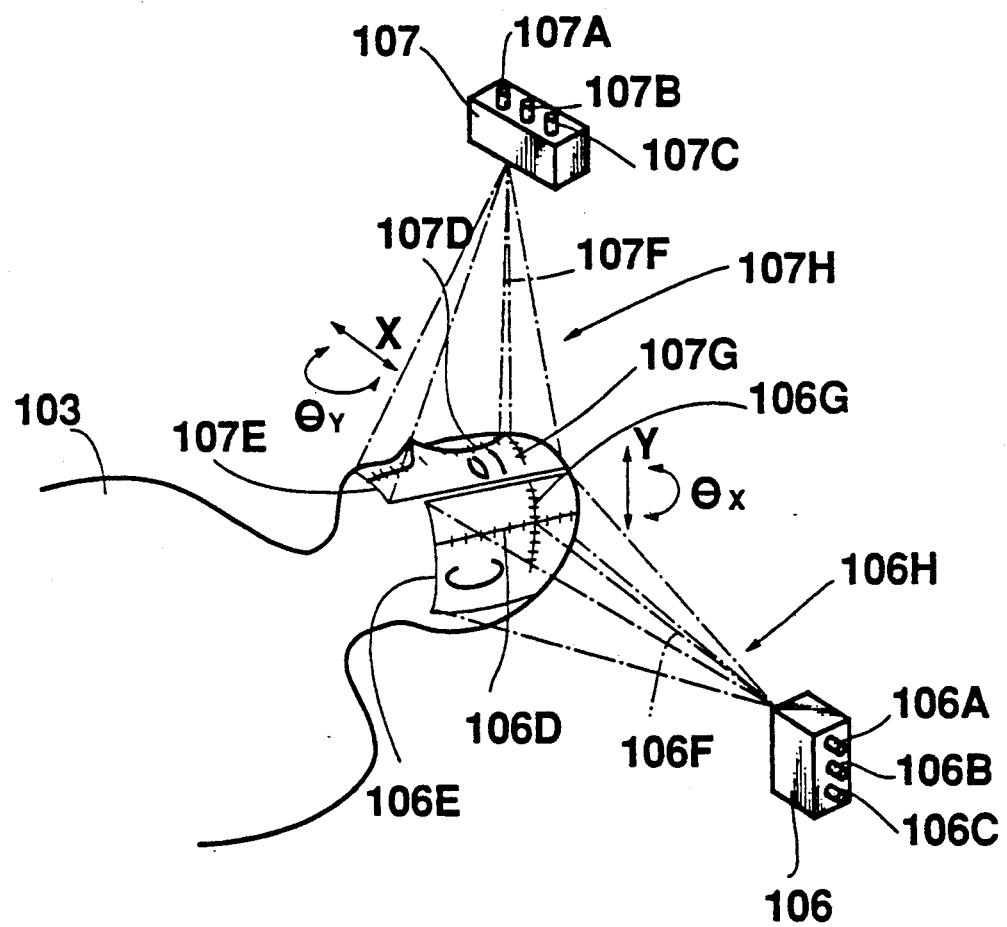
FIG. 5 is an illustration of the operation of the embodiment of an apparatus for setting multi-slice imaging conditions.

The illuminations by the first and second projectors 106 and 107 are provided for the purpose of determining the position of a part of the patient 103 to be imaged. As shown in FIG. 5, the first projector 106 projects an X cross-shaped beam 106H along a first projection plane and within a first projection area which beam can be inclined by an angle $\theta x$ with respect to the first projection plane in a Y-direction, and the second projector 107 projects a Y cross-shaped beam 107H along a second projection plane and within a second projection area which beam can be inclined by an angle $\theta y$ with respect to the second projection plane in an X-direction. The X cross-shaped beam 106H makes an X cross-shaped image 106D along an X projection plane 106E, with an X projection axis 106F as a center and with X scale marks 106G (indicating specific distance intervals such as 10 mm) superposed on the side of the patient 103. The Y cross-shaped beam 107H makes a Y cross-shaped image 107D along a Y projection plane 107E, with a Y projection axis 107F as a center and with Y scale marks 107G (also indicating the same specific distance intervals as the X scale marks 106G) superposed, on the top of the patient 103.

Figure 6:
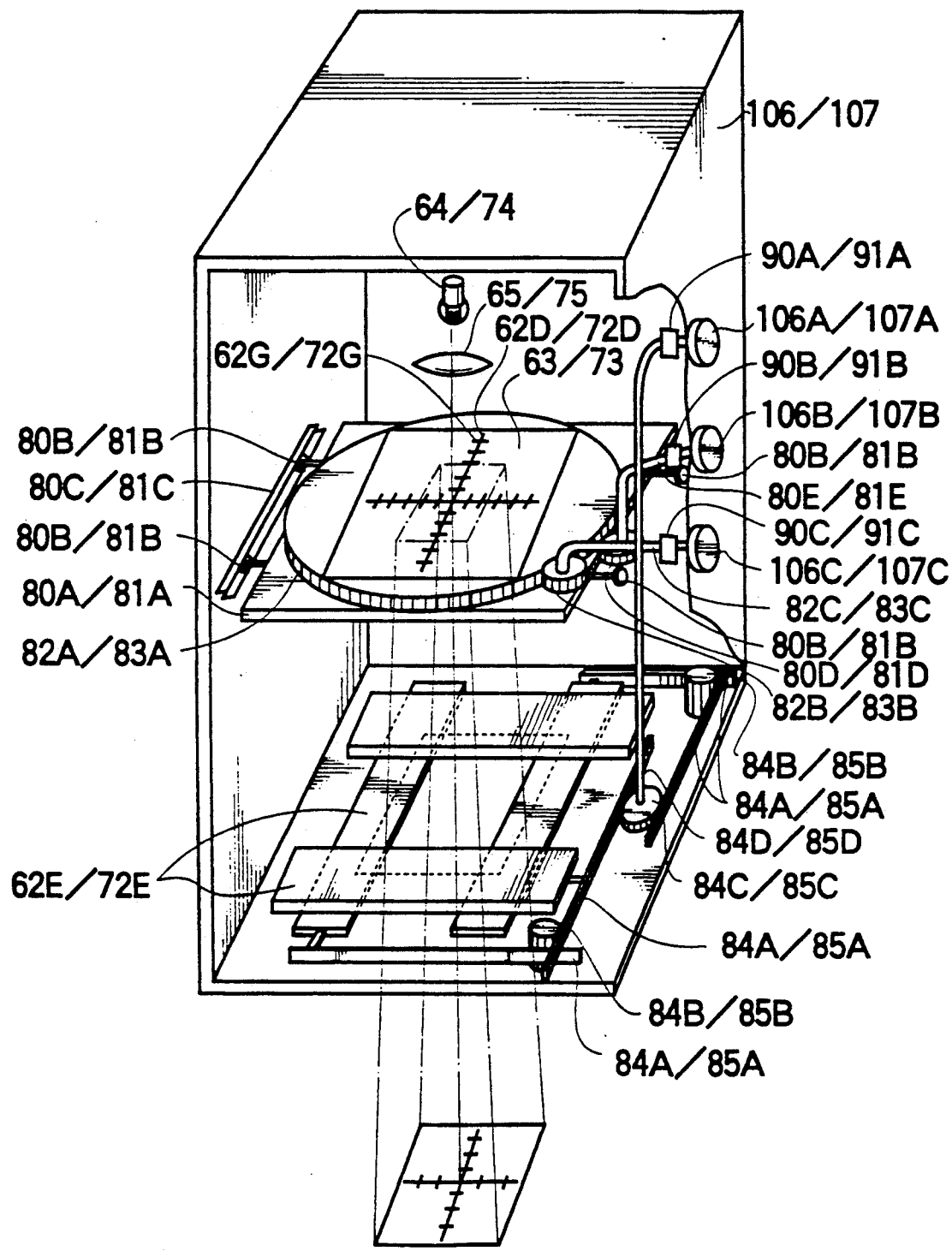
FIG. 6 is a cutaway view of a projector of the embodiment of an apparatus for setting multi-slice imaging conditions.

A more detail configuration of both the first and second projectors 106 and 107 is shown in FIG. 6.

As shown, the first projector 106 comprises a fixed light source 64, a fixed lens 65, a transparent glass plate 63 with dark lines 62D and 62G corresponding to the X cross image 106D and X scale marks 106G, and non-transparent edging plates 62E for defining the projection area 106E, such that the light beam from the light source 64 which is focused by the lens 65 can be projected through the transparent glass plate 63 and the prejection area 106E defined by the non-transparent edging plates 62E onto the patient 103 to be imaged.

In addition, the first projector 106 further comprises a moving mechanism for moving the transparent glass plate 63 with respect to the non-transparent edging plates 62E; an inclining mechanism for inclining the transparent glass plate 63 relative to the projection plane; a projection area changing mechanism for changing the projection area 106E by moving the non-transparent edging plates 62E; a potentiometer 90B attached to the moving mechanism for detecting the position of the transparent glass plate 63 with respect to the non-transparent edging plates 62E; another potentiometer 90A attached to the inclining mechanism for detecting the angle of inclination of the transparent glass plate 63 relative to the projection plane; and still another potentiometer 90A attached to the projection area changing mechanism for detecting the area of the projection plane.

The moving mechanism includes a rectangular plate 80A having a rack on one side and in which the transparent glass plate 63 is embedded; rollers 80B attached to two sides of the rectangular plate 80A and slidable along rails 80C provided on two inner side walls of the first projector 106; a pinion 80D engaged with the rack of the rectangular plate 80A; and a flexible wire 80E for connecting the pinion 80D and the first projection moving knob 106B and communicating the rotation of the first projection moving knob 106B to the pinion 80D, where the potentiometer 90B is attached on the flexible wire 80E.

The inclining mechanism includes a circular plate 82A having a rack on its circumference, rotatably mounted on the rectangular plate 80A, and in which the transparent glass plate 63 is also embedded; a pinion 82B engaged with the rack of the circular plate 82A; and a flexible wire 82C for connecting the pinion 82B and the first projection inclining knob 106C and communicating the rotation of the first projection inclining knob 106C to the pinion 82B, where the potentiometer 90C is attached on the flexible wire 82C.

The projection area changing mechanism includes two pairs of guiding rods 84A one of the pair being attached to one of the longitudinal ones of the non-transparent edging plates 62E, while the other one of the pair being attached to one of the transverse ones of the non-transparent edging plates 62E, and each of the pair having a rack on one side; two guiding pinions 84B each of which is engaged with the racks of one of the pairs of guiding rods 84A; a pinion 84C engaged with the racks of both of the pairs of guiding rods 84A; and a flexible wire 84D for connecting the pinion 84C and the first projection area changing knob 106A and communicating the rotation of the first projection area changing knob 106A to the pinion 84C, where the potentiometer 90A is attached on the flexible wire 84D.

The second projector 107 has a similar configuration, as indicated by corresponding components for the second projector 107 represented by lablels appearing after the slash in FIG. 6.

In correspondence with this inner configuration, the first projector 106 has the first projection area changing knob 106A for allowing the operator to move the non-transparent edging plates 62E thereby changing the first projection area, the first projection moving knob 106B for allowing the operator to move the transparent glass plate 63 thereby moving the first projected image within the first projection area, and the first projection inclining knob 106C for allowing the operator to incline the transparent glass plate 63 thereby inclining the first projected image relative to the first projection plane. Similarly, the second projector 107 has the second projection area changing knob 107A for allowing the operator to move the non-transparent edging plates 72E thereby changing the second projection area, the second projection moving knob 107B for allowing the operator to move the transparent glass plate 73 thereby moving the second projected image within the second projection area, and the second projection inclining knob 107C for allowing the operator to incline the transparent glass plate 73 thereby inclining the second projected image relative to the second projection plane.

Figure 7:
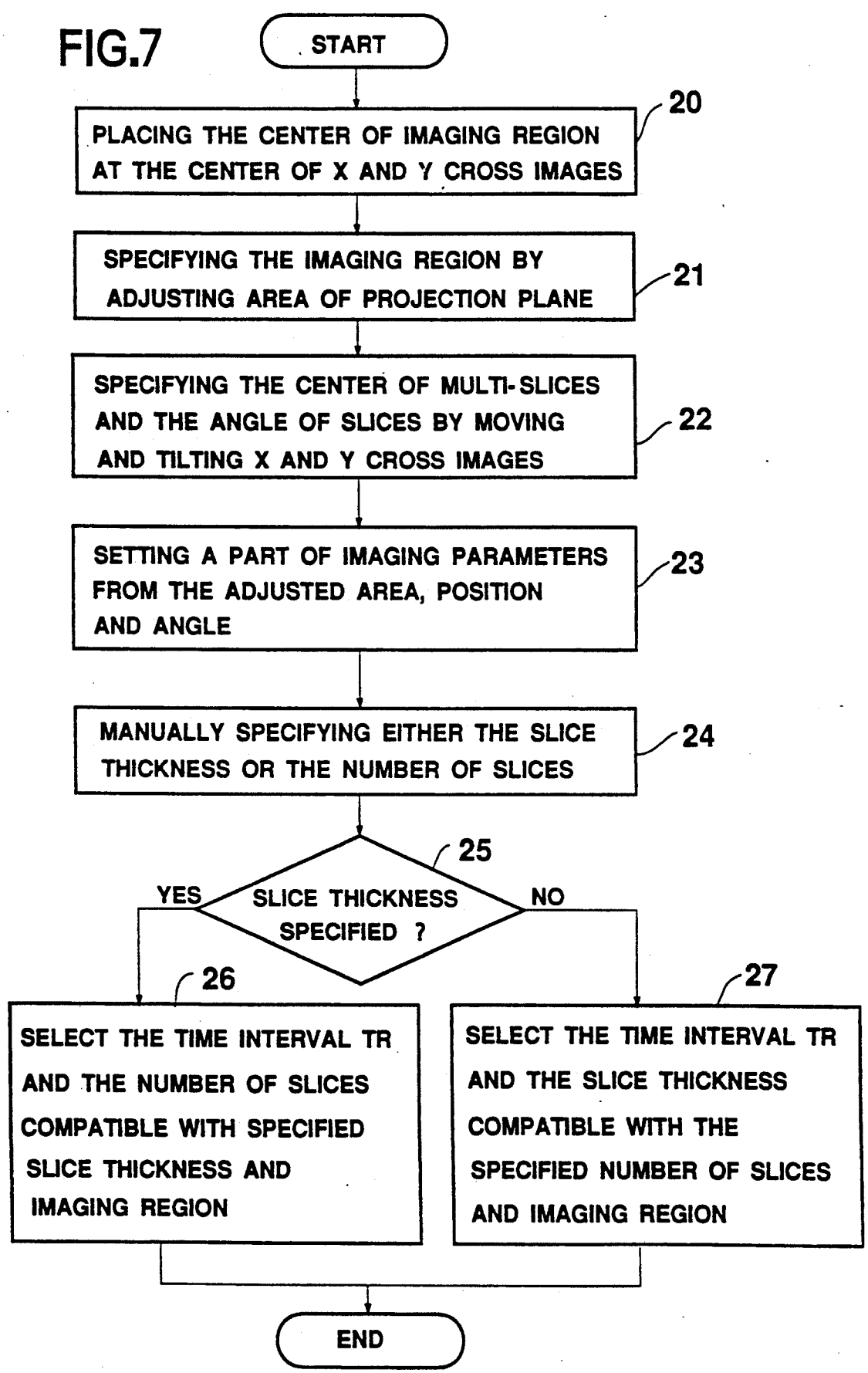
FIG. 7 is a flow chart for the operation of setting the multi-slice imaging condition by the embodiment of an apparatus for setting multi-slice imaging conditions.

Now, the operation of multi-slice imaging by this computed tomographic imaging system will be explained with reference to FIG. 7.

First, at the step 20 the top plate 104 and the lift 105 are adjusted manually through the control panel 108 such that the center of the part of the patient 103 to be imaged meets with the centers of the X and Y cross images 106D and 107D.

Next, the imaging region is set as follows. At the step 21 the area of imaging region is specified by the projection plane 106E/107E, while at the step 22 the position of the center of multi-slices and the angle of slices are specified by moving and inclining the X cross image 106D and Y cross image 107D. Here, when setting the imaging region on a plane perpendicular to the sagittal plane (Y-Z plane), the first projector 106 will be utilized, whereas when setting the imaging region on a plane perpendicular to the coronal plane (X-Z plane), the second projector 107 will be utilized.

Once this adjusting of the projection plane 106E/107E and cross image 106D/107D is completed, the area, position, and angle will be detected by the potentiometers in the first and second projectors 106 and 107, and the information on the detected area, position, and angle are transmitted through the transmission line 112 to the control unit 110, so that the imaging parameters such as the view field, position of the center of the multi-slices, slicing angle, and slicing plane, can be specified and set on a basis of the transmitted information, in a conventionally known manner, at the step 23.

Meanwhile, at the step 24 either the slice thickness or the number of slices is manually specified by the operator from the operation unit 109.

When what was manually entered at the step 24 is determined by the control unit 110 at the step 25 to be the slice thickness, the control unit 110 automatically calculates an appropriate imaging time interval TR and a number of slices compatible with the specified slice thickness and the imaging region at the step 26.

More specifically, when a slice thickness of 10 mm is specified for an imaging region of 150 mm thickness, and the time required for imaging each slice is assumed to be 160 ms, then in order to cover the imaging region with 150 mm thickness at one imaging, it is necessary to have 15 slices because 150 mm/10 mm=15 slices, which requires $160 \times 15 = 2400$ ms for the imaging time interval TR. Thus, in this case the control unit 110 automatically sets the imaging time interval TR to 2400 ms and the number of slices is set to be 15.

Alternatively, when what was manually entered at the step 24 is determined by the control unit 110 at the step 25 to be the number of slices, the control unit 110 automatically calculates at the step 27 an appropriate slice thickness and the imaging time interval TR compatible with the specified number of slices and the imaging region size.

More specifically, when the number of slices is specified as 12 for the imaging region of 150 mm thickness, and the time required for each slice is assumed to be 160 ms, then in order to cover the 150 mm imaging region in one imaging. it is necessary to have 12.5 mm thickness for each slice because 150 mm/12 slices=12.5 mm. At the same time, an imaging time interval TR for which 12 slices is the maximum possible number of slices, such as 2000 ms. Thus, in this case the control unit 110 automatically sets the slice thickness to 12.5 mm and the imaging time interval TR is set to be 2000 ms.

This completes the setting of the multi-slice imaging conditions, so that a desired multi-slice imaging in a desired imaging region can now be taken in one imaging.

Thus, according to this embodiment, it is possible to take a desired multi-slice imaging in a desired imaging region in one imaging because a part of the imaging conditions can automatically be set to be consistent with the other manually specified imaging conditions, by providing a mechanism for freely setting the projection area and utilizing the detected projection area in determining the part of the imaging conditions automatically. As a result, no initial scanning imaging is necessary according to this embodiment, and the task of setting the imaging conditions required for the operator can be eased.

In addition, because the transparent glass plates 63 in both the first and second projector 106 and 107 can be inclined, it is possible to take multi-slice imaging on both a plane perpendicular to the coronal plane and a plane perpendicular to the sagittal plane.

Furthermore, the X and Y scale marks 106G and 107G facilitate an easy visual determination of the necessary number of slices.

It is to be noted that a part of the imaging conditions may be pre-set to predetermined initial values in the apparatus, instead of being manually entered as in the above embodiment.

It is also to be noted that a choice for a part of the imaging conditions to be specified and a remaining part of the imaging conditions to be calculated can be changed from those used in the description of the above embodiment, without departing from the essence of the present invention, so long as the determination of the remaining part of the imaging conditions is carried out by utilizing the detected projection area and the specified part of the imaging conditions.

It is also obvious that the above embodiment can be modified by making the various knobs on the first and second projectors 106 and 107 also controllable from the operation unit 109, so that all the manual specification of the imaging conditions and parameters can be performed on the operation unit 109. For example, the knobs may be equipped with actuating means which actuates the knobs in response to control signals from the control unit 109.

Also, the projection plane 106E/107E can be replaced by a projection boundary indicating a boundary of the imaging region, not entire imaging region.

Figure 8:
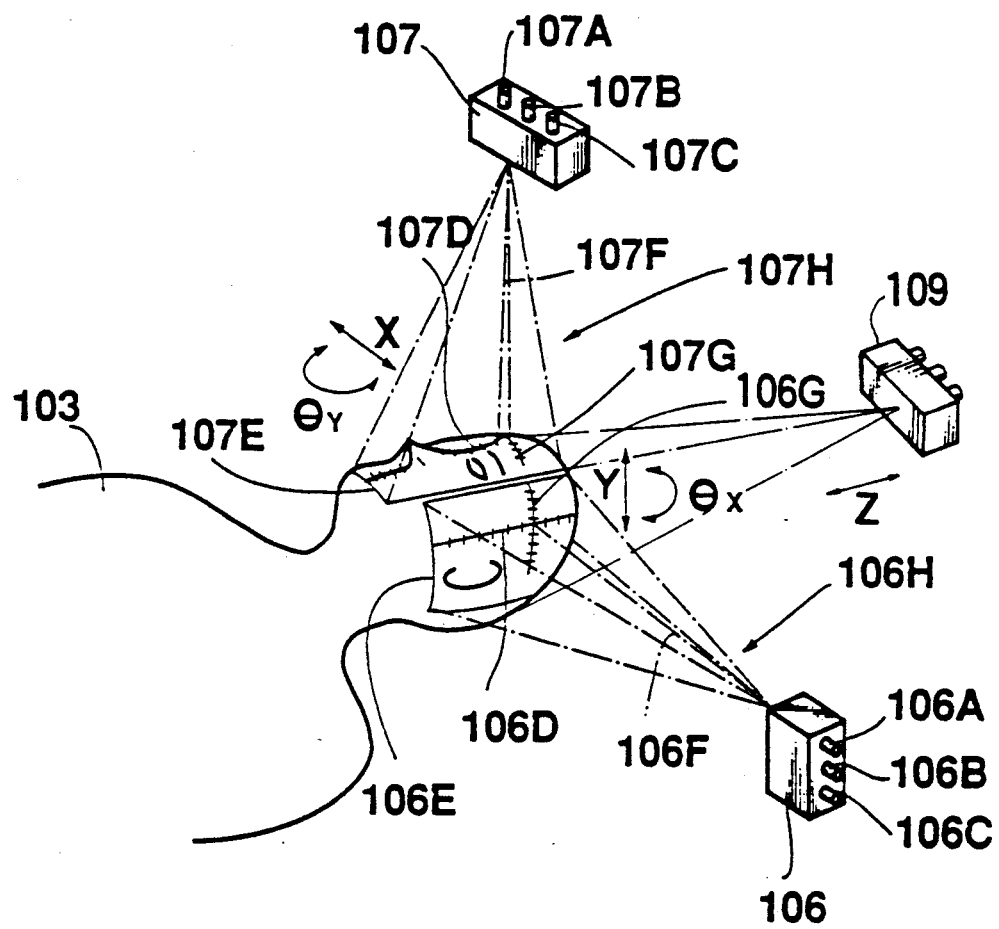
FIG. 8 is a perspective view of an apparatus for setting multi-slice imaging conditions according to another embodiment of the present invention.

Also, as shown in FIG. 8, by providing a third projector 109 similar to the first and second projector 106 and 107 on the Z-axis, a multi-slice imaging on a plane perpendicular to the axial plane can also be made possible. The third projector 109 can be fixed relative to the frame 101 by using an appropriate attaching means, such as a supporting arm which has one end attached to the frame 101 and the other end extending to a position on the Z-axis behind the bore 101A at which the third projector 109 can be supported.

It is further to be noted that the above embodiment can readily be modified for an X-ray CT apparatus in which the relation between scanning interval and possible number of scanning for a continuous scanning is determined by the heat capacity of X-ray tubes.

Besides these, various modifications and variations of the above embodiment may be made without departing from the novel and advantageous features of the present invention. Accordingly, all such modifications and variations are intended to be included within the scope of the appended claims.

What is claimed is:

1. An apparatus for setting multi-slice imaging conditions in a computed tomographic imaging system, comprising:
    projector means for illuminating an object to be imaged within at least one projection area defined along at least one projection plane, said projection plane and said projection area corresponding to an imaging region;
    projection area changing means for changing the projection area;
    projection area detecting means for detecting the projection area;
    input means for specifying one of the multi-slice imaging conditions including an imaging time interval, a slice thickness, and a number of slices; and
    processing means for determining unspecified ones of the multi-slice imaging conditions in accordance with the one of the multi-slice imaging conditions specified by the input means and the detected projection area.

2. The apparatus of claim 1, wherein the input means comprises means for allowing an operator to manually specify one of a slice thickness and a number of slices; and wherein the processing means determines an imaging time interval and the number of slices if the slice thickness is specified by the operator, said imaging time interval and said number of slices being determined in accordance with the manually specified slice thickness and the detected projection area, and determines the slice thickness and the imaging time interval if the number of slices is specified by the operator, said slice thickness and said imaging time interval being determined in accordance with the manually specified number of slices and the detected projection area.

3. The apparatus of claim 1, wherein the projector means includes:
    a first projector means for illuminating an object to be imaged within a first projection area defined along a first projection plane; and
    a second projector means for illuminating an object to be imaged within a second projection area defined along a second projection plane; said second projection plane being orthogonal to the first projection plane.

4. The apparatus of claim 3, wherein the projector means further includes third projector means for illuminating an object to be imaged within a third projection area defined along a third projection plane, said third projection plane being orthogonal to both the first and second projection 5. An apparatus for setting multi-slice imaging conditions in a computed tomographic imaging system, comprising:
    projector means for illuminating an object to be imaged within at least one projection area defined along at least one projection plane, said projection plane and said projection area corresponding to an imaging region;

projection area changing means for changing the projection area;

projection area detecting means for detecting the projection area;

input means for specifying one of the multi-slice imaging conditions including an imaging time interval, a slice thickness, and a number of slices; and processing means for determining unspecified ones of the multi-slice imaging conditions in accordance with the one of the multi-slice imaging conditions specified by the input means and the detected projection area;

wherein the projector means includes:

means for superposing at least one cross-shaped image having an orientation along one of said at least one projection plane by projecting at least one cross-shaped beam onto the object to be imaged;

means for moving the cross-shaped image within the projection area;

means for inclining the cross-shaped image relative to the projection plane;

means for detecting a position of the cross-shaped image within the projection area; and means for detecting an inclined angle of the cross-shaped image relative to the projection plane.

6. The apparatus of claim 5, wherein the cross-shaped image is defined by scale marks for indicating equidistant intervals.

7. A method of setting multi-slice imaging conditions in a computed tomographic imaging system, comprising the steps of:

illuminating an object to be imaged within at least one projection area defined along at least one projection plane, said projection plane and projection area corresponding to an imaging region;

changing the projection area;

detecting the projection area;

specifying one of the multi-slice imaging conditions including an imaging time interval, a slice thickness, and a number of slices; and determining unspecified ones of the multi-slice imaging conditions in accordance with the specified one of the multi-slice imaging conditions and the detected projection area.

8. The method of claim 7, wherein the specifying step comprises the steps of manually specifying one of a slice thickness and a number of slices; and wherein at the determining step, an imaging time interval and the number of slices are determined if the slice thickness is specified, said imaging time interval and said number of slices being determined in accordance with the manually specified slice thickness and the detected projection area, and the slice thickness and the imaging time interval are determined if the number of slices is specified, said slice thickness and said imaging time interval being determined in accordance with the manually specified number of slices and the detected projection area.

9. The method of claim 7, wherein the illuminating step includes:

a first step of illuminating an object to be imaged within a first projection area defined along a first projection plane; and a second step of illuminating the object to be imaged within a second projection area defined along a second projection plane, said second projection plane being orthogonal to the first projection plane.

10. The method of claim 9, wherein the illuminating step further includes a third step of illuminating the object to be imaged within a third projection area defined along a third projection plane, said third projection plane being orthogonal to both the first and second projection planes.

11. A method of setting multi-slice imaging conditions in a computed tomographic imaging system, comprising the steps of:

illuminating an object to be imaged within at least one projection area defined along at least one projection plane, said projection plane and projection area corresponding to an imaging region;

changing the projection area;

detecting the projection area;

specifying one of the multi-slice imaging conditions including an imaging time interval, a slice thickness, and a number of slices; and determining unspecified ones of the multi-slice imaging conditions in accordance with the specified one of the multi-slice imaging conditions and the detected projection area;

wherein the illuminating step includes the steps of:

superposing a cross-shaped image having an orientation along one of said at least one projection plane by projecting at least one cross-shaped beam onto the object to be imaged;

moving the cross-shaped image within the projection area;

inclining the cross-shaped image relative to the projection plane;

detecting a position of the cross-shaped image within the projection area; and detecting an angle of inclination of the cross-shaped image relative to the projection plane.

12. The method of claim 11, wherein the step of superposing a cross-shaped image uses a cross-shaped image having scale marks for indicating equidistant intervals.

* * * * *